United States Patent
Cole et al.

(10) Patent No.: US 12,258,350 B1
(45) Date of Patent: Mar. 25, 2025

(54) CRYSTALLINE FORMS OF 4-ETHOXY-N-(2-METHOXYETHYL)-N-METHYL-3-(5-METHYL-4-OXO-7-PROPYL-3,4-DIHYDROIMIDAZO[5,1-F][1,2,4]TRIAZIN-2-YL)BENZENESULFONAMIDE

(71) Applicant: Retension Pharmaceuticals, Inc., Falls Church, VA (US)

(72) Inventors: Bridget McCarthy Cole, Quincy, MA (US); Enoch Kim, Marblehead, MA (US); Dhanapalan Nagarathnam, Marblehead, MA (US); Paul Sweetnam, Marblehead, MA (US)

(73) Assignee: Retension Pharmaceuticals, Inc., Falls Church, VA (US)

( * ) Notice: Subject to any disclaimer, the term of this patent is extended or adjusted under 35 U.S.C. 154(b) by 0 days.

(21) Appl. No.: 18/948,031

(22) Filed: Nov. 14, 2024

(51) Int. Cl.
*A61K 31/53* (2006.01)
*C07D 253/10* (2006.01)
*C07D 487/04* (2006.01)

(52) U.S. Cl.
CPC ............ *C07D 487/04* (2013.01); *A61K 31/53* (2013.01)

(58) Field of Classification Search
CPC ............................. A61K 31/53; C07D 253/10
USPC ......................................... 514/243; 544/184
See application file for complete search history.

(56) References Cited

U.S. PATENT DOCUMENTS 8,853,394 B2 * 10/2014 Campbell ................ A61P 9/10
544/184

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — Elmore Patent Law Group, P.C.; Joseph C. Zucchero; Carolyn S. Elmore

(57) ABSTRACT

The present invention provides solid, crystalline forms of Compound I. Compound I has the structure:

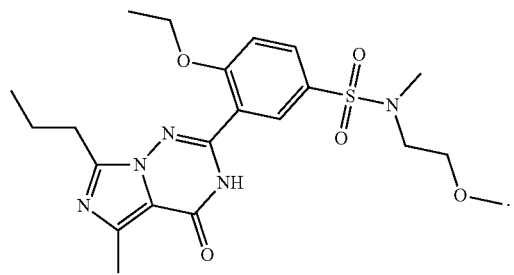

The invention further provides methods for treating, preventing, or reducing a disease or disorder in a subject in need thereof, the methods comprising administering to the subject an effective amount of a crystalline form of Compound I. The disease or disorder may include any chronic disease and/or cardiovascular condition related to or caused by high blood pressure.

15 Claims, 1 Drawing Sheet

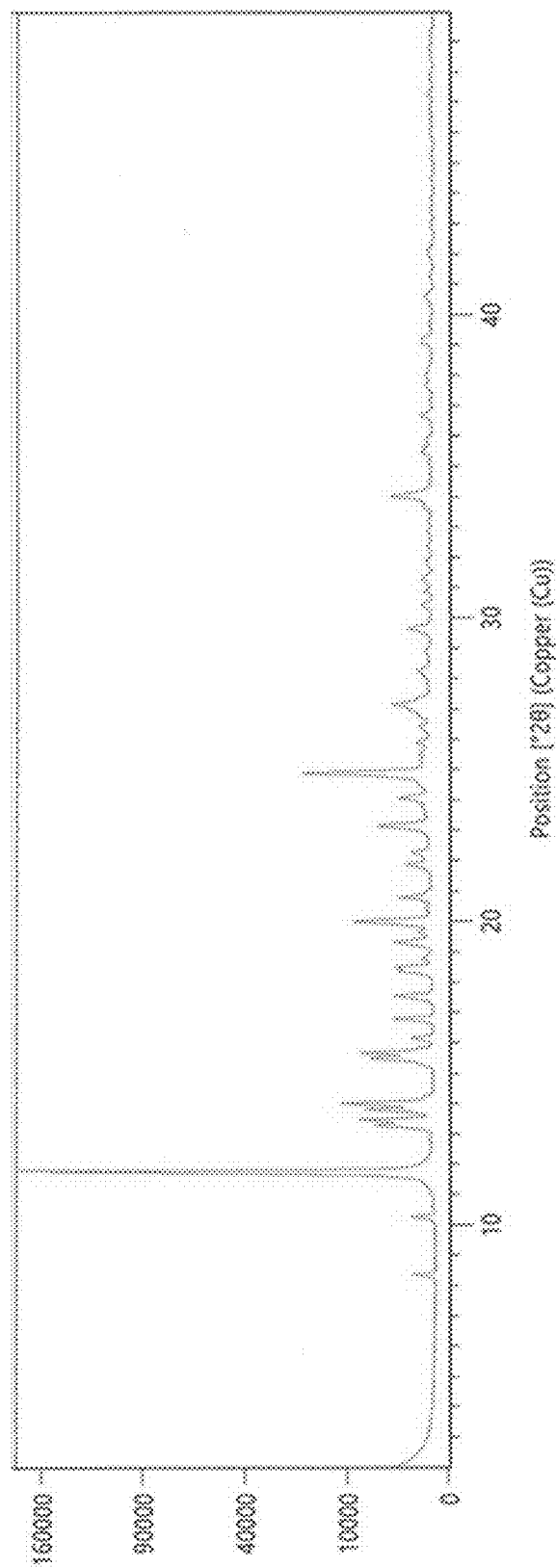

CRYSTALLINE FORMS OF 4-ETHOXY-N-(2-METHOXYETHYL)-N-METHYL-3-(5-METHYL-4-OXO-7-PROPYL-3,4-DIHYDRO-IMIDAZO[5, 1-F][1,2,4]TRIAZIN-2-YL) BENZENESULFONAMIDE

BACKGROUND OF THE INVENTION

The physiological and clinical effects of inhibitors of cyclic guanosine 3',5'-monophosphate specific phosphodiesterase (cGMP-specific PDE) suggest that such inhibitors have utility in a variety of disease states in which modulation of smooth muscle, renal, hemostatic, inflammatory, and/or endocrine function is desired. Type 5 cGMP-specific phosphodiesterase (PDE5) is the major cGMP hydrolyzing enzyme in vascular smooth muscle. Thus, an inhibitor of PDE5 may be indicated in the restoration or maintenance of endothelial and cardiovascular health and treatment of cardiovascular disorders, including but not limited to hypertension, cerebrovascular disorders, and disorders of the urogenital system, particularly erectile dysfunction.

Although pharmaceutical drugs that provide selective inhibition of PDE5 are currently available, for example, vardenafil (marketed under the trade name Levitra®) is a potent and selective inhibitor of PDE5 and is currently indicated for the treatment of erectile dysfunction, there is a present need to improve the pharmacokinetic properties of PDE5 inhibitors to treat diseases and conditions associated with PDE5 activity that currently marketed PDE5 inhibitors are not efficacious in treating.

SUMMARY OF THE INVENTION

Provided herein is a crystalline form of a PDE5 inhibitor useful for the treatment of a subject in need thereof. In an aspect, provided herein is a crystalline form of Compound I having the formula:

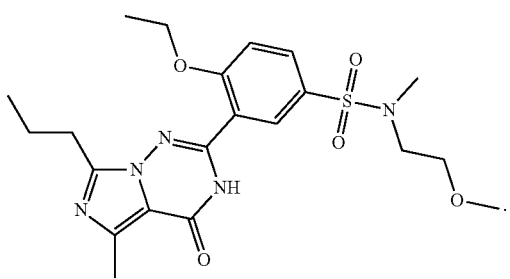 [SMILES: CCCc1nc(C)c2c(=O)[nH]c(-c3cc(S(=O)(=O)N(C)CCOC)ccc3OCC)nn12]

Additionally, the present invention relates to methods for treating, preventing, or reducing a disease or disorder in a subject in need thereof. In embodiments, the disease or disorder includes any chronic disease and/or cardiovascular condition related to or caused by high blood pressure. The methods comprise administering to the subject an effective amount of a crystalline form of Compound I.

BRIEF DESCRIPTION OF THE DRAWING

The invention is illustrated, but in no way limited, by the tables herein and the following examples, with reference to the figure in which:

FIG. 1 is an experimental PXRD diffractogram for a crystalline form of Compound I (Form A).

DETAILED DESCRIPTION

Definitions

Listed below are definitions of various terms used to describe the crystalline forms provided herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which the compound and its crystalline forms belong.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, "addiction" is generally defined as a chronic brain disease that causes compulsive drug seeking and use, or alcohol seeking and use. Drug addiction can be opioid addiction (i.e., opioid dependence), stimulant addiction, and the like.

As used herein, the term "pharmaceutically acceptable carrier" refers to a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the present disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound provided herein, and not injurious to the patient.

Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound provided herein, and are physiologically acceptable to the patient. Supplementary active compounds may also be incorporated into the compositions. Other additional ingredients that may be included in the pharmaceutical compositions used in the practice of the present disclosure are known in the art and described, for example in Remington's Pharmaceutical Sciences (Genaro, Ed., Mack Publishing Co., 1985, Easton, PA), which is incorporated herein by reference.

As used herein, the term "treat," "treated," "treating," or "treatment" includes the diminishment or alleviation of at least one symptom associated or caused by the state, disorder or disease being treated. In certain embodiments, the treatment comprises bringing into contact with the opioid receptor an effective amount of the compound provided herein for conditions related to opioid dependence, alcohol dependence or addiction.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. In an embodiment, the patient, subject, or individual is human.

The term "administering "or "administration" and the like, refers to providing a therapeutic agent, such as a crystalline form disclosed herein, to the subject in need of treatment. In an embodiment, the subject is a mammal. In another embodiment, the subject is a human.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of +20% or +10%, including+5%, +1%, and +0.1% from the specified value, as such variations are appropriate to perform the disclosed methods.

Characterization of Crystalline Form

Provided herein are solid, crystalline forms of Compound I. Compound I has the structure:

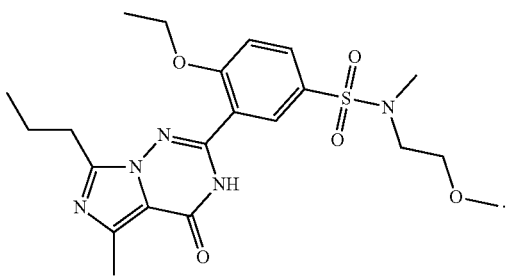 [SMILES: CCCc1nc(C)c2c(=O)[nH]c(-c3cc(S(=O)(=O)N(C)CCOC)ccc3OCC)nn12]

The PDE inhibitor of Compound I is preferred as it distributes preferentially to vascular tissue and provides a significant anti-hypertensive response as a single agent in a hypertension therapy resistant population. PDE inhibitors useful in the practice of the invention, as well as method of making, also include those disclosed in U.S. Pat. Nos. 8,299,083.

The solid state of a compound can be important when the compound is used for pharmaceutical purposes. The physical properties of a compound can change from one solid form to another, which can affect the suitability of the form for pharmaceutical use. For example, a particular crystalline solid compound can overcome the disadvantage of other solid forms of the compound such as, e.g., physical instability and/or reduced purity.

As with all pharmaceutical compounds and compositions, the chemical and physical properties of the crystalline form of compound I utilized can be important in commercial development and manufacturing. These properties include, but are not limited to: (1) packing properties such as molar volume, density and hygroscopicity, (2) thermodynamic properties such as melting temperature, vapor pressure and solubility, (3) kinetic properties such as dissolution rate and stability (including stability at ambient conditions, especially to moisture, and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, processing and storage of pharmaceutical compositions comprising compound I.

The crystalline form provided herein can be characterized by, for example, powder X-ray diffraction (PXRD). The crystalline form described herein is identifiable on the basis of characteristic peaks in a powder X-ray diffraction analysis. Powder X-ray diffraction (PXRD) is a scientific technique using X-ray, neutron, or electron diffraction on powder, microcrystalline, or other solid materials for structural characterization of solid materials. Powder x-ray diffraction (PXRD) diffractograms can be obtained using, for example, a PANalytical X'Pert PRO MPD diffractometer using an incident beam of Cu radiation produced using an Optix long, fine-focus source. An elliptically graded multilayer mirror was used to focus Cu Kα x-rays through the specimen and onto the detector.

PXRD diffractograms of Compound I obtained by the methods described herein are shown in the Examples and Figure. The PXRD data provided herein is obtained by a method utilizing Cu Kα radiation. The crystalline form of the invention is not limited to those made in accordance with the methods described herein.

In one embodiment, the crystalline form of Compound I disclosed herein is characterized by a PXRD diffractogram having peaks expressed in degrees 2-theta at angles (±0.2 degrees) of 11.7626, 14.0190, 20.0045, and 24.8947.

In another embodiment, the crystalline form of Compound I is characterized by a PXRD diffractogram having peaks expressed in degrees 2-theta at angles (±0.2 degrees) of 13.4699, 13.8105, 15.4971, and 15.6786.

In another embodiment, the crystalline form of Compound I is characterized by a PXRD diffractogram having peaks expressed in degrees 2-theta at angles (±0.2 degrees) of 11.7626, 13.4699, 13.8105, 14.0190, 15.4971, 15.6786, 20.0045, and 24.8947.

In another embodiment, the crystalline form of Compound I is characterized by a PXRD diffractogram having peaks expressed in degrees 2-theta at angles (±0.2 degrees) of 11.7626, 13.2893, 13.4699, 13.8105, 14.0190, 15.4971, 15.6786, 20.0045, 23.1513, 24.0973, 24.8947, and 34.0159.

In another embodiment, the crystalline form of Compound I is characterized by a PXRD diffractogram having peaks expressed in degrees 2-theta at angles (±0.2 degrees) of 11.7626, 13.2893, 13.4699, 13.8105, 14.0190, 15.4971, 15.6786, 16.7928, 17.5616, 19.3294, 20.0045, 20.7937, 23.1513, 24.0973, 24.8947, 27.1547, and 34.0159.

In another embodiment, the crystalline form of Compound I has a PXRD diffractogram substantially as depicted in FIG. 1. In one embodiment, the crystalline form of Compound I is characterized by a PXRD diffractogram having peaks expressed in degrees 2-theta at angles (±0.2 degrees) as shown in FIG. 1.

In one embodiment, the crystalline form of Compound I is characterized by any two, three, four, five, six, seven, or eight peaks as shown in Table 1. In another embodiment, the crystalline form of Compound I is characterized by a PXRD diffractogram having peaks expressed in degrees 2-theta at angles (±0.2 degrees) as shown in Table 1.

TABLE 1

| Peak Number | Angle (degrees 2θ) |
|---|---|
| 1 | 8.3647 |
| 2 | 10.2792 |
| 3 | 11.7626 |
| 4 | 13.2893 |
| 5 | 13.4699 |
| 6 | 13.8105 |
| 7 | 14.0190 |
| 8 | 15.4971 |
| 9 | 15.6786 |
| 10 | 16.1763 |
| 11 | 16.7928 |
| 12 | 17.5616 |
| 13 | 18.3924 |
| 14 | 18.5060 |
| 15 | 19.3294 |
| 16 | 20.0045 |
| 17 | 20.7937 |
| 18 | 21.8819 |
| 19 | 22.2703 |
| 20 | 23.1513 |
| 21 | 24.0973 |
| 22 | 24.8947 |
| 23 | 26.9752 |
| 24 | 27.1547 |
| 25 | 29.6558 |
| 26 | 34.0159 |

The invention further provides methods for treating, preventing, or reducing a disease or disorder in a subject in need thereof. The disease or disorder includes any chronic disease and/or cardiovascular condition related to or caused by high blood pressure. The methods of the present invention comprise administering to the subject an effective amount of a crystalline form of Compound I.

The methods of the present invention can be employed for the maintenance and/or the restoration of endothelial and cardiovascular health. The methods of the present invention can be employed for the treatment of conditions where the inhibition of phosphodiesterases, particularly PDE5, would be beneficial. For example, the methods of the invention may be used for the treatment of cardiovascular disorders, cerebrovascular disorders, and disorders of the urogenital system. Cardiovascular disorders include, but are not limited to, hypertension, isolated systolic hypertension (ISH), pulmonary hypertension, acute heart failure, chronic heart failure, ischemic heart disease (including, but not limited to chronic angina), peripheral arterial disease, pre-eclampsia, Raynaud's Disease, endothelial dysfunction/pre-hypertension, chronic obstructive pulmonary disease (COPD), Meniere's disease, or neuropathic pain in diabetes. Disorders of the urogenital system include, but are not limited to, benign prostatic hypertrophy, erectile dysfunction, and female sexual dysfunction. Preferably the cardiovascular disorder is hypertension. Preferably, the disorder of the urogenital system is erectile dysfunction.

In particular, the present invention relates to a method for treating, preventing, or reducing hypertension in a subject in need thereof, the method comprising administering to the subject an effective amount of a crystalline form of Compound I.

In embodiments, the present invention also relates to a method treating, preventing, or reducing diseases and/or conditions caused by or associated with hypertension in a subject in need thereof, the method comprising administering to the subject an effective amount of a crystalline form of Compound I. Such diseases and/or conditions caused by or associated with hypertension include, but are not limited to, primary hypertension, secondary hypertension, resistant hypertension, pregnancy-related hypertensive disorder, pulmonary hypertension, renal hypertension, angina, and coronary heart disease.

The term "pharmaceutically effective amount", "therapeutically effective amount", and "effective amount" are used interchangeably and generally refers to an amount sufficient to affect a desired biological effect, such as a beneficial result, in at least a sub-population of cells in an animal at a reasonable benefit/risk ratio applicable to any medical treatment, e.g. reasonable side effects applicable to any medical treatment. Thus, an effective amount will depend upon the context in which it is being administered. An effective amount may be administered in one or more prophylactic or therapeutic administrations.

Pharmaceutical Compositions

In another aspect, provided are pharmaceutically acceptable compositions which comprise a therapeutically-effective amount of the crystalline form of Compound I, formulated together with one or more pharmaceutically acceptable carriers (additives) and/or diluents. As described in detail below, the pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The pharmaceutical formulations may be immediate release or sustained release formulations. Methods for preparing immediate release and sustained release formulations are well known to those of skill in the art.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5)

malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain compounds may contain a basic functional group, such as amino alkylamino or imidazole, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of the PDE5 inhibitors. These salts can be prepared in situ in the administration vehicle or the dosage form manufacturing process, or by separately reacting a purified compound of the PDE5 inhibitor in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the PDE5 inhibitors may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of PDE5 inhibitors. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the crystalline form of Compound I include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, from about 5 percent to about 70 percent, or from about 10 percent to about 30 percent.

In certain embodiments, a formulation comprising the crystalline form of Compound I also comprises an excipient selected from the group consisting of cyclodextrins, celluloses, liposomes, micelle forming agents, e.g., bile acids, and polymeric carriers, e.g., polyesters and polyanhydrides; and the crystalline form of Compound I. In certain embodiments, an aforementioned formulation renders orally bioavailable the crystalline form of Compound I.

Methods of preparing these formulations or compositions include the step of bringing into association the crystalline form of Compound I with the carrier and, optionally, one or more accessory ingredients. In general, the formulations are prepared by uniformly and intimately bringing into association the crystalline form of Compound I with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the crystalline form of Compound I as an active ingredient. The crystalline form of Compound I may also be administered as a bolus, electuary or paste.

In solid dosage forms for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated foam, if appropriate, with one or more of the above-described excipients.

Liquid dosage forms for oral administration of the crystalline form of Compound I include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal or vaginal administration may be presented as a suppository, which may be prepared by mixing one or more compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical or transdermal administration of the crystalline form of Compound I include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to the crystalline form of Compound I, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the crystalline form of Compound I, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the crystalline form of Compound I to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated.

Pharmaceutical compositions suitable for parenteral administration comprise the crystalline form of Compound I in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the crystalline form of Compound I is administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the crystalline form of Compound I, which may be used in a suitable hydrated form, and/or the pharmaceutical compositions, are formulated into pharmaceutically-acceptable dosage forms by conventional methods known to those of skill in the art.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds employed in the pharmaceutical composition at levels lower than that required in order to achieve the desired therapeutic effect and gradually increase the dosage until the desired effect is achieved.

In general, a suitable daily dose of the crystalline form of Compound I will be that amount of the compound which is the lowest dose effective to produce a therapeutic effect. Such an effective dose will generally depend upon the factors described above. Generally, oral, intravenous, and subcutaneous doses of the compounds, when used for the indicated effects, will range from about 0.1 to about 300 mg. In other embodiments, the doses will be 5, 10, 20, 30, 40, 50, 60, 70, 80, 90, 100, 125, 150, 175, 200, 225, 250, 275 or 300 mg depending on the ability of the crystalline form of Compound I to partition to the vasculature.

If desired, the effective daily dose of the active compound may be administered as two, three, four, five, six or more sub-doses administered separately at appropriate intervals throughout the day, optionally, in unit dosage forms. Preferred dosing is one administration per day.

In certain embodiments, a controlled release formulation comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and copolymers thereof, celluloses, polypropylene, polyethylenes, polystyrene, polymers of lactic acid and glycolic acid, polyanhydrides, poly(ortho) esters, poly(butic acid), poly (valeric acid), poly(lactide-co-caprolactone), polysaccharides, proteins, polyhyaluronic acids, polycyanoacrylates, and blends, mixtures, or copolymers thereof.

The release characteristics of a formulation depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Kits

Also provided are kits comprising a container comprising the crystalline form of Compound I and instructions for administering the crystalline form. Such kits may comprise a box with appropriate labeling and containers such as bottles, vials, tubes and the like. Appropriate labeling includes directions for administering the crystalline form of Compound I to treat hypertension. In one embodiment, the crystalline form of Compound I is packaged in a unit dose form.

In another embodiment, the instructions comprise treating a patient with hypertension. In another embodiment, the crystalline form of Compound I is present in the kit at a dose of 0.1 to 300 mg. In another embodiment, the crystalline form of Compound I is present in the kit at a dose of 10, 20, 30, 40, 50, 60, 70, 80, 90, 100, 125, 150, 175, 200, 225, 250, 275 or 300 mg. In another embodiment, the crystalline form of Compound I is formulated as part of a pharmaceutical composition comprising a pharmaceutically acceptable carrier. In another embodiment, the pharmaceutical composition is an immediate release composition. In another embodiment, the pharmaceutical composition is a sustained release composition. In another embodiment, the sustained release pharmaceutical composition releases the crystalline form of Compound I over a period of 4-24 hours. In another embodiment, the sustained release pharmaceutical composition releases the crystalline form of Compound I over a period of 4-8, 4-12, 8-12 or 12-24 hours.

EXAMPLES

The crystalline form of the invention was made as described below. The resulting material was then analyzed using the analytical techniques described herein, that is, powder X-ray diffraction.

Analytical Methods

The crystalline form of Compound I was obtained according to the following method: A solution of Compound I (1 equiv.) in ethanol (6 volumes) is heated to reflux (75-80° C.) and stirred for 10-15 minutes. Heptane (32 volumes) is slowly added to the solution over 15-30 minutes at 65-80° C. The solution is slowly cooled to 25-30° C. over 1-2 hours and stirred at this temperature for 1-1.5 hours to induce crystallization. The product is filtered from solution and washed with heptane (6 volumes). The product is then dried to constant weight under vacuum at 60-70° C. for 10-14 hours.

X-ray powder diffraction pattern is obtained on a Panlytical instrument (Model-Empyrean) operating with Cu Kα/b radiation at 45 kV and 40 mA using a PIXcel1PD-Medipix3 scanning line detector. The powder diffraction pattern of the sample is obtained from 2 to 50° 2θ at a rate of 1° 2θ/48 seconds. Raw data files are collected and processed using HighScore software.

The relative intensity of each diffractogram peak in Table 1 as well as FIG. 1 may change or shift under certain conditions, although the crystalline form is the same. One of ordinary skill in the art should be able to readily determine whether a given crystalline form is the same crystalline form as described in FIG. 1 or Table 1.

While this invention has been particularly shown and described with references to preferred embodiments thereof, it will be understood by those skilled in the art that various changes in form and details may be made therein without departing from the scope of the invention encompassed by the appended claims.

What is claimed:
1. A crystalline form of Compound I:

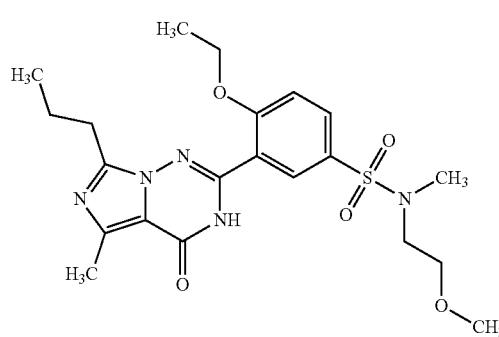

wherein the crystalline form is characterized by a powder X-ray diffraction (PXRD) diffractogram comprising characteristic peaks (° 2θ) at angles of 11.7626° ±0.2° 2θ, 14.0190° ±0.2° 2θ, 20.0045° ±0.2° 2θ, and 24.8947° ±0.2° 2θ.

2. The crystalline form of claim 1, wherein the crystalline form is further characterized by a PXRD diffractogram comprising characteristic peaks (° 2θ) at angles of 13.4699° ±0.2° 2θ, 13.8105° ±0.2° 2θ.

3. The crystalline form of claim 2, wherein the crystalline form is further characterized by a PXRD diffractogram comprising characteristic peaks (° 2θ) at angles of 13.2893° ±0.2° 2θ, 23.1513° ±0.2° 2θ.

4. The crystalline form of claim 3, wherein the crystalline form is further characterized by a PXRD diffractogram comprising characteristic peaks (° 2θ) at angles of 16.7928° ±0.2° 2θ, 17.5616° ±0.2° 2θ.

5. The crystalline form of claim 4, wherein the crystalline form is further characterized by the PXRD diffractogram as depicted in FIG. 1.

6. A pharmaceutical composition comprising a pharmaceutically acceptable carrier and the crystalline form of claim 1.

7. A method for inhibiting phosphodiesterase 5 (PDE5) activity in a subject in need thereof, wherein the method comprises administering to the subject a therapeutically effective amount of the crystalline form of claim 1.

8. The method of claim 7, wherein the subject has any one of the following:
   (a) a chronic disease related to or caused by high blood pressure; or
   (b) a cardiovascular condition related to or caused by high blood pressure; or
   (c) a chronic disease related to or caused by high blood pressure and a cardiovascular condition related to or caused by high blood pressure.

9. The method of claim 7, wherein the subject has hypertension.

10. A method for inhibiting phosphodiesterase 5 (PDE5) activity in a subject in need thereof, wherein the method comprises administering to the subject a therapeutically effective amount of the crystalline form of claim 5.

11. The method of claim 10, wherein the subject has any one of the following:
    (a) a chronic disease related to or caused by high blood pressure; or
    (b) a cardiovascular condition related to or caused by high blood pressure; or
    (c) a chronic disease related to or caused by high blood pressure and a cardiovascular condition related to or caused by high blood pressure.

12. The method of claim 10, wherein the subject has hypertension.

13. A method for inhibiting phosphodiesterase 5 (PDE5) activity in a subject in need thereof, wherein the method comprises administering to the subject a therapeutically effective amount of the pharmaceutical composition of claim 6.

14. The method of claim 13, wherein the subject has any one of the following:
    (a) a chronic disease related to or caused by high blood pressure; or
    (b) a cardiovascular condition related to or caused by high blood pressure; or
    (c) a chronic disease related to or caused by high blood pressure and a cardiovascular condition related to or caused by high blood pressure.

15. The method of claim 13, wherein the subject has hypertension.

* * * * *

UNITED STATES PATENT AND TRADEMARK OFFICE
CERTIFICATE OF CORRECTION

PATENT NO. : 12,258,350 B1
APPLICATION NO. : 18/948031
DATED : March 25, 2025
INVENTOR(S) : Bridget McCarthy Cole et al.

It is certified that error appears in the above-identified patent and that said Letters Patent is hereby corrected as shown below:

In the Claims

Column 15, Claim 2, Line 4: please add --, 15.4971° + 0.2 °2θ, and 15.6786° + 0.2 °2θ-- before the ".";
Column 15, Claim 3, Line 8: please add --, 24.0973° + 0.2 °2θ, and 34.0159° + 0.2 °2θ-- before the "."; and
Column 15, Claim 4, Line 12: please add --, 19.3294° + 0.2 °2θ, 20.7937° + 0.2 °2θ, and 27.1547° + 0.2 °2θ-- before the ".".

Signed and Sealed this
Thirteenth Day of May, 2025

Coke Morgan Stewart
*Acting Director of the United States Patent and Trademark Office*